United States Patent [19]

Woodhour et al.

[11] 4,069,313

[45] Jan. 17, 1978

[54] WATER-IN-OIL ADJUVANT COMPOSITION

[75] Inventors: Allen F. Woodhour, Horsham; Maurice R. Hilleman, Lafayette Hill, both of Pa.

[73] Assignee: Merck & Co., Inc., Rahway, N.J.

[21] Appl. No.: 674,360

[22] Filed: Apr. 7, 1976

Related U.S. Application Data

[60] Division of Ser. No. 525,149, Nov. 19, 1974, Pat. No. 3,983,228, which is a continuation-in-part of Ser. No. 392,402, Aug. 28, 1973, abandoned, which is a continuation of Ser. No. 233,815, March 10, 1972, abandoned, which is a continuation-in-part of Ser. No. 141,401, May 7, 1971, abandoned.

[51] Int. Cl.$^2$ .................... A61K 39/18; A61K 39/12; A61K 47/00

[52] U.S. Cl. ....................................... 424/89; 424/88; 424/92; 424/365

[58] Field of Search ...................... 424/89, 365, 88, 92

[56] References Cited

U.S. PATENT DOCUMENTS

| 3,149,036 | 9/1964 | Woodhour et al. ................. 424/89 |
| 3,435,112 | 3/1969 | Kuhns et al. ........................ 424/89 |

*Primary Examiner*—Sam Rosen
*Attorney, Agent, or Firm*—Donald J. Perrella

[57] ABSTRACT

Pure isomannide monooleate and pure aluminum monostearate are used singularly or in combination in the preparation of emulsion type adjuvant vaccines to yield an adjuvant superior to prior art adjuvants which employ commercial mannide monooleate and aluminum monostearate. Highly desirable formulations are obtained by the inclusion of pure aluminum monostearate as a stabilizer in combination with the pure isomannide monooleate.

11 Claims, No Drawings

WATER-IN-OIL ADJUVANT COMPOSITION

This application is a division of application Ser. No. 525,149, filed Nov. 19, 1974, now U.S. Pat. No. 3,983,228, which in turn is a continuation-in-part of copending Ser. No. 392,402, filed Aug. 28, 1973, now abandoned, which is in turn a continuation of Ser. No. 233,815, filed Mar. 10, 1972, now abandoned, which is in turn a continuation-in-part of Ser. No. 141,401, filed May 7, 1971, now abandoned.

This invention is concerned with pure isomannide monooleate, and its use as an emulsifying agent, particularly in the preparation of water-oil emulsions for use as adjuvants in vaccine formulations. The invention further relates to pure aluminum monostearate as an emulsion stabilizer for water-oil emulsions. Of particular interest are adjuvant compositions which contain pure isomannide monooleate and pure aluminum monostearate. The novel adjuvant compositions of the invention may be employed as vehicles for the administration of injectable immunological substances and thereby produce higher antibody titers than are obtainable by the use of an equivalent aqueous dose thereof.

The invention further relates to improved vaccine formulations containing said adjuvant vehicles.

Broadly considered, the vaccines utilized at the present time are "fluid vaccines." The term "fluid vaccine" designates a suspension of an immunogenic or desensitizing agent in water or in a medium comprising a single, aqueous, liquid phase. Such vaccines are subject to the criticism that induced immunity is neither sufficiently good nor long-lasting following one or two vaccine injections having a reasonable dose volume. Many fluid vaccines must therefore be administered in a number of injections over a period of a few weeks or more if the desired protection is to be obtained. Additionally, combinations of a number of antigens in a single vaccine with a reasonable dose volume is not easily possible with normal fluid vaccines. Attempts have been made to overcome these difficulties by employing adjuvants to potentiate the activity of the fluid vaccines.

The principal purpose for employment of an immunologic adjuvant is to achieve a more durable immunity of a higher lever employing a smaller antigenic mass in a fewer number of doses than could be achieved by administration of the equivalent aqueous antigen. It may be noted that development of an immunologically satisfactory and pharmacologically acceptable adjuvant is a prime essential for the preparation of workable multivalent killed virus vaccines which are effective and practical in the prevention of viral, bacterial, mycoplasmal or rickettsial diseases.

The prior art emulsion type adjuvants that have been employed to enhance the antigenicity of parenteral vaccines are comprised, in general, of emulsions of mineral or vegetable oils and water, either the oil or water being the continuous phase and the discontinuous phase being either water, oil or a second water-oil emulsion. The emulsion adjuvants generally require for stability other components known as emulsifying agents. A commonly employed emulsifying agent in the prior art is commercial mannide monooleate. For example, U.S. Pat. No. 3,149,036, the disclosure of which is incorporated herein by reference, describes the preparation of water-in-oil emulsion type adjuvants comprising as emulsifier commercial "mannide monooleate." The adjuvant formulation reported in the patent also includes commercially available aluminum monostearate as an emulsion stabilizer.

The novel emulsion type adjuvants of the invention possess unexpected advantages over the prior art adjuvants including those reported in U.S. Pat. No. 3,149,036. For example, adjuvants composed of pure isomannide monooleate and pure aluminum monostearate possess superior emulsion characteristics when compared to the corresponding adjuvants utilizing chemically impure materials. Furthermore, the novel adjuvants of this invention demonstrate distinct advantages in their ease of preparation relative to the prior art adjuvants.

It has further been found that the novel adjuvants of the invention unexpectedly permit the incorporation of higher concentrations of proteinaceous antigen than may be obtained with adjuvants composed of relatively impure components. This desirable property enables the highly efficient adjuvants of the invention to be employed with a wider range of immunological materials than would be possible with adjuvants containing impure components.

In addition to the above advantages, the novel adjuvants of the invention also demonstrate storage stability superiority compared to the prior art adjuvants. Furthermore, the adjuvants utilizing pure materials have the ability of withstanding deemulsification as a result of excessive energy input during the emulsification process and thereby offer significant advantages to the commercial emulsification technology by contributing simplicity and economy to said process.

As an added advantage, use of pure isomannide monooleate and aluminum monostearate leads to product consistency which is extremely important in the medicament field, whereas commercial mannide monooleate, and aluminum monostearate being a complex mixture of varying composition, may deny the requisite product consistency.

The novel adjuvants of the invention may be employed to potentiate the antibody response of antigenic materials. The term "antigen" and "antigenic material" which are used interchangeably herein include one or more non-viable immunogenic or desensitizing (antiallergic) agents of bacterial, viral or other origin. The antigen component of the products of the invention may consist of a dried powder, an aqueous solution, an aqueous suspension and the like, including mixtures of the same, containing a non-viable immunogenic or desensitizing agent or agents.

The specific oil employed in the novel adjuvant composition of the invention is not critical. Any physiologically acceptable injectable oil or mixtures thereof including those oils which satisfy the specifications of the U.S. Pharmacopeia or National Formulary may be utilized in the practice of the invention. Representative members include peanut oil, safflower oil, soya bean oil, cottonseed oil, mineral oils of a pharmaceutical grade such as light liquid paraffin and light mineral oil, chaulmoogra oil, corn oil, persic oil, olive oil, sesame oil, almond oil, castor oil, squalane, isopropyl myristate and coconut oil. Of particular preference are peanut oil and highly purified light mineral oil.

When the adjuvant composition of this invention is employed as a vehicle for an immunological substance, the antigen (or antigens) is preferably incorporated in the aqueous phase prior to the addition of the aqueous phase to the oil. The immunological agent advantageously is used in purified or concentrated form. It may be a dried solid, or an adsorbate on a parenterally acceptable adsorbant, for example aluminum phosphate, aluminum hydroxide, pumice or kieselguhr.

The aqueous phase may conveniently be comprised of the antigenic material in a parenterally acceptable liquid. For example, the aqueous phase may be in the form of a vaccine in which the antigen is dissolved in a balanced salt solution, physiological saline solution, phosphate buffered saline solution, tissue culture fluids or other media in which the organism may have been grown. The aqueous phase also may contain preservatives and/or substances conventionally incorporated in vaccine preparations. The adjuvant emulsions of the invention may be prepared employing techniques well known to the art.

The antigen may be in the form of purified or partially purified antigen derived from bacteria, viruses, rickettsia or their products, or extracts of bacteria, viruses, or rickettsia, or the antigen may be an allergen such as pollens, dusts, danders, or extracts of the same or the antigen may be in the form of a poison or a venom derived from poisonous insects or reptiles. In all cases the antigens will be in the form in which their toxic or virulent properties have been reduced or destroyed and which when introduced into a suitable host will either induce active immunity by the production therein of antibodies against the specific micro-organisms, extract or products of microorganisms used in the preparation of the antigen, or, in the case of allergens, they will aid in alleviating the symptoms of the allergy due to the specific allergen. The antigens can be used either singly or in combination; for example, multiple bacterial antigens, multiple viral antigens, multiple mycoplasmal antigens, multiple rickettsial antigens, multiple bacterial or viral toxoids, multiple allergens or combinations of any of the foregoing products can be combined in the aqueous phase of the adjuvant composition of this invention. Antigens of particular importance are derived from bacteria such as *B. pertussis, Leptospira pomona* and *icterohaemorrhagiae, S. typhosa, S. paratyphi A and B, C. diphtheriae, C. tetani, C. botulinum, C. perfringens, C. feseri* and other gas gangrene bacteria, *B. anthracis, P. pestis, P. multocida, V. cholerae, Neisseria meningitidis, N. gonorrheae, Hemophilus influenzae, Treponema pollidum,* and the like; from viruses as polio virus (multiple types), adeno virus (multiple types), parainfluenza virus (multiple types), measles, mumps, respiratory syncytial virus, influenza (various types), shipping fever virus (SF$_4$), Western and Eastern equine encephalomyelitis, Japanese B. encephalomyelitis, Russian Spring Summer encephalomyelitis, hog cholera virus, Newcastle disease virus, fowl pox, rabies, feline and canine distemper and the like viruses, from rickettsiae as epidemic and endemic typhus or other members of the spotted fever group, from various spider and snake venoms or any of the known allergens for example from ragweed, house dust, pollen extracts, grass pollens and the like.

The relative proportions of the pure isomannide monooleate and pure aluminum monostearate as components of an adjuvant composition are not critical. Effective adjuvant compositions may be achieved employing, by volume, from about 0.5-10% of emulsifier (pure isomannide monooleate), 0.5 to 10% emulsion stabilizer (pure aluminum monostearate) and 80-99% oil vehicle. Of particular preference are adjuvant systems containing 1-6% aluminum monostearate (preferably 4%) and 1-10% isomannide monooleate (preferably 6%), the remainder being the oil vehicle. Vaccine products which contain an aqueous antigen component as the disperse aqueous phase may contain, by volume, from about 10-90% of adjuvant material, the preferred vaccine formulation containing about 50% aqueous antigen phase and about 50% adjuvant composition.

Pure isomannide monooleate, has the structure

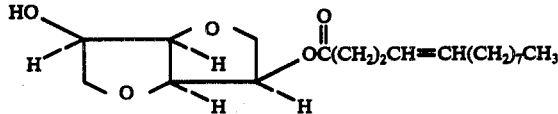

and the following characteristics:
Specific Rotation: $[\alpha]D^{25} + 66.7°$ (C = 1.0, CHCl$_3$)
Refractive Index: $n_D^{22}$ 1.4780
Saponification equivalent: 99.7% of theory
Boiling Point: 220° C/0.200 mmHg.
Molecular Distillation: 105°-111° C/<1 μ.Hg.
Mass Spectrum: m/e = 410
NMR Spectrum in (d$_6$ — dimethyl sulfoxide)
δ  0.9-2.2  [Multiplet, 31H, CH$_3$(CH$_2$)$_7$—CH=CH=(CH$_2$)$_7$]
δ 3.1-5.05 Multiplet, 9H

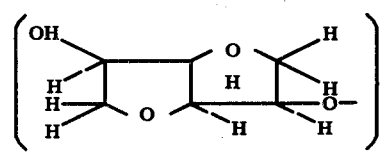

δ 5.3 (Triplet, 2H, —CH=CH—)

| IR Spectrum | |
| --- | --- |
| Wave No. (cm$^{-1}$) | Intensity |
| 3444 | Medium |
| 3000 | " |
| 2920 | Strong |
| 2850 | " |
| 1740 | " |
| 1650 | Very weak |
| 1470 | Medium |
| 1240 | " |
| 1170 | " |
| 1120 | " |
| 1080 | " |
| 1060 | " |
| 1020 | " |

The process for the preparation of pure isomannide monooleate can be described by the following equation:

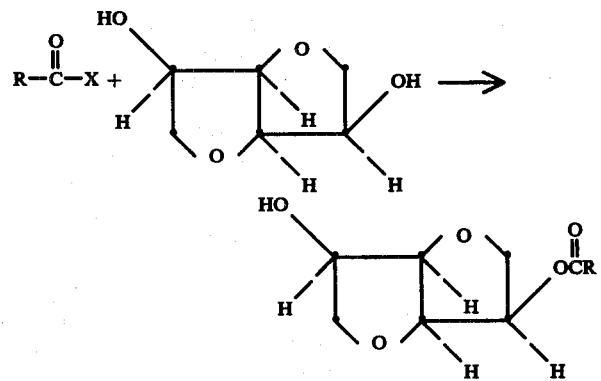

wherein

R is $CH_3(CH_2)_7CH=CH(CH_2)_7-$

X is OH; halo such as bromo, chloro or iodo; lower alkoxy of 1 to about 4 carbon atoms such as methoxy, ethoxy, propoxy, or butoxy; or mononuclear aryloxy, preferably phenoxy;

The reaction conditions may vary depending on the nature of the X substituent.

Where X is halo, the oleoyl halide is added to an excess of isomannide dissolved in an inert solvent such as acetone; an aromatic hydrocarbon such as benzene, toluene, xylene or the like; an ether such as tetrahydrofuran, dioxane, 1,2-dimethoxyethane or the like; or a halogenated hydrocarbon such as 1,2-dichloroethane, chloroform, methylene chloride or the like. The temperature of the reaction can be anywhere between about $-20°$ C. and the reflux temperature of the solvent. Where the temperature is elevated, above about $50°$ C., the reaction proceeds readily without the presence of an acid acceptor. At the lower temperatures it is advantageous to have present a base such as an alkali or alkaline earth carbonate or bicarbonate, pyridine, a tertiary amine such as triethylamine, N,N-dimethylaniline or 1,4-diazabicyclo[2,2,2]octane.

Where X is hydroxyl, a mixture of oleic acid, an excess of isomannide, and preferably an acid catalyst are allowed to react in a solvent. The catalyst can be any strong mineral acid such as sulfuric, hydrochloric, perchloric, hydrobromic, hydrofluoric, chlorosulfonic and ethanesulfonic acid; an acid regenerated cation exchange resin; various salts of mercury, silver, cobalt, nickel and cerium; or aromatic sulfonic acids such as benzenesulfonic, p-toluenesulfonic, or $\beta$-naphthalenesulfonic acid. The solvent employed is generally an aromatic solvent or halogenated aromatic solvent such as benzene, toluene, xylene, chlorobenzene or the like. The reaction is conducted at any temperature from about ambient to the reflux temperature of the solvent employed.

Where X is lower alkoxy or aryloxy, a mixture of approximately equal molar quantities of the oleic acid ester and isomannide are reacted together preferably in the presence of a catalytic amount of a base or an acid. The reaction may be conducted in a solvent such as an aromatic hydrocarbon, or an ether such as tetrahydrofuran, dioxane, 1,2-dimethoxyethane or the like at any temperature between about $-20°$ C. and the reflux temperature of the solvent. The catalyst is preferably an alkali metal alkoxide and preferably, but not necessarily, the alkoxy portion of the oleic ester and of the catalyst are the same. Alternatively, a strong mineral acid such as sulfuric, sulfonic or hydrochloric acid may be employed. The reaction may also be conducted in the absence of a solvent in which case the mixture of the two reactants and an alkali metal alkoxide are heated to above the fusion point preferably at a reduced pressure to distill off the alcoholic by-product.

The following examples are provided for illustrative purposes and may include particular features of the invention; however, the examples should not be construed as limiting the invention, variations of which are possible without departing from the spirit or scope thereof.

EXAMPLE 1

Isomannide Monooleate from Oleoyl Chloride and Isomannide

Oleoyl chloride (10 g., 0.0332 mole) was added to a refluxing solution of 14.6 g., 0.0996 mole of isomannide is 200 ml. of toluene. The mixture was refluxed for two hours and cooled to room temperature. Unreacted isomannide was removed by filtration and the filtrate was washed with 25 ml. of saturated sodium bicarbonate and 25 ml. of water. The volume of toluene was reduced to 70 ml. by distillation at atmospheric pressure. The toluene solution was passed through a bed of alumina and the eluant distilled to give isomannide monooleate bp $226°/0.300$ mm. Hg., thin layer chromatography (silica gel; 3 hexane:1 ethyl acetate) showed a single spot with $R_f 0.25$; vapor phase chromatography indicated purity greater than 99%.

EXAMPLE 2

Isomannide Monooleate from Oleic acid and Isomannide

A mixture of 4.0 g. (0.014 mole) of oleic acid, 6.12 g. (0.042 mole) of isomannide and 0.4 g. (0.002 mole) of p-toluenesulfonic acid in 120 ml. of toluene was refluxed for 12 hours during which time water was removed employing a water separator. After cooling, the reaction mixture was filtered with the aid of diatomaceous earth and concentrated in vacuo. The residue was treated with 25 ml. of hexane. The insoluble isomannide was removed by filtration and the filtrate was passed through a bed of alumina to remove p-toluenesulfonic acid and oleic acid. The filtrate was distilled in vacuo to give isomannide monooleate, bp $220°$ C./0.200 mg. Hg.

EXAMPLE 3

Isomannide Monooleate from Methyl Oleate and Isomannide

A mixture of 5.93 g. (0.02 mole) of methyl oleate, 8.77 g. (0.02 mole) of isomannide and 0.0524 g. (0.001 mole of sodium methoxide was heated in vacuo (25–50 mm. Hg.) at $100°$ C. for 1 hour. The melt was cooled to room temperature. The oily solid was treated with 40 ml. of hexane. The isomannide was removed by filtration and the filtrate was distilled in vacuo to give isomannide monooleate, bp $218°-222°$ C./0.175 mm. Hg.

When pure aluminum monostearate is employed as the emulsion stabilizer component of an adjuvant composition the virologist is assured that the vaccine formulation will be safe and have the product consistency demanded of a parenteral dosage form as distinguished from the uncertainties inherent in a relatively impure material. In accordance with the instant invention the skilled artisan is provided a stabilizer of known constant composition that may be reproduced upon demand. Pure aluminum monostearate may be prepared from high purity stearic acid, sodium hydroxide and potassium aluminum sulfate. The product precipitates from hot aqueous solution and contains one atom of aluminum per molecule of stearic acid.

It has been found that reaction of one mole of stearic acid, one mole of alum ($KAl(SO_4)_2.12H_2O$) and 3 moles of sodium hydroxide in hot dilute aqueous solution gives a product which, after filtration, washing, and drying, analyzes for $Al(OH)_2(OOC(CH_2)_{16}CH_3)$. The reaction is run hot to keep sodium stearate in solution and is run in dilute solution to minimize absorption of inorganic salts. Three moles of caustic are used to give a pH near 7.

It should be noted that the pure aluminum monostearate prepared below is in sharp contrast with the available article of commerce which is a gross mixture of fatty acid radicals, some batches containing more palmitate than stearate.

EXAMPLE 4

Pure Aluminum Monostearate

Stearic acid 99.95% pure (90.0 g., 0.316 mole) was added to a solution of 38.0 g. (0.316 mole) of sodium hydroxide in 6.3 liter of water. The mixture was heated to 90° C. A solution of aluminum potassium sulfate (alum) in 6.3 liter of water was heated to 50° C and added over 20 minutes to the hazy solution. The temperature of the reaction mixture was maintained at 80° ±2° during the addition. Solid precipitated after about 60–70% of the alum solution was added. After the addition was complete, the heterogeneous mixture was cooled to 25° over 3 hours and 15 minutes and then to 5° over 1 hour and 45 minutes. The mixture was aged at 5° for 30 minutes and filtered. The product was slurry washed with 7 × 1 liter of water to remove sulfate. The last two washes gave a negative $SO_4^=$ test (barium chloride). The cake as air dried overnight and then dried in vacuo at 100° to constant weight. 107.2 Grams (99%) of aluminum monostearate (LOD 0.6%) was collected.

Anal. Calc. for $C_{18}H_{37}O_4Al$: C, 62.76; H, 10.83; Al, 7.83. Found: C, 63.13; H, 11.03; Al, 8.04.

EXAMPLE 5

Preparation of Peanut oil adjuvant using pure isomannide monooleate at 10, 6, 4 and 2% and pure aluminum monostearate at 4%

|  | Percent by Volume | | | |
|---|---|---|---|---|
| Peanut Oil | 86 | 90 | 92 | 94 |
| Pure aluminum monostearate | 4 | 4 | 4 | 4 |
| Pure isomannide monooleate | 10 | 6 | 4 | 2 |

Sterile isomannide monooleate is added to sterile peanut oil and thoroughly mixed. The bivalent oil-isomannide monooleate vehicle is added to pure sterile aluminum monostearate. The trivalent mixture is solubilized by elevating the temperature to about 120° C. with constant agitation to insure thorough dispersion of the pure aluminum monostearate in the bivalent oil vehicle. The mixture is permitted to cool to room temperature (20°–30° C.).

EXAMPLE 6

Preparation of Peanut Oil Adjuvant Influenza Vaccines with Pure Isomannide Monooleate at 5, 3, 2 and 1% and Pure Aluminum Monostearate at 2%

The peanut oil adjuvant obtained in Example 5 is used to prepare an influenza vaccine by emulsifying it with an equal volume of a phosphate buffered saline solution containing 2800 CCA units/ml. of bivalent influenza virus (1600 CCA units/ml. $A_2$/Aichi/2/68 and 1200 CCA units/ml. of B/Mass./3/66).

EXAMPLE 7

Preparation of Mineral Oil Adjuvant using pure isomannide monooleate at 5, 3, 2 and 1%

|  | Percent by volume | | | |
|---|---|---|---|---|
| Mineral Oil | 90 | 94 | 96 | 98 |
| Pure Isomannide monooleate | 10 | 6 | 4 | 2 |

Sterile isomannide monooleate is added to sterile mineral oil and thoroughly mixed.

EXAMPLE 8

Preparation of Mineral Oil adjuvant vaccine with Pure Isomannide monooleate at 5, 3, 2 and 1%

The mineral oil adjuvant from Example 7 is used to prepare an influenza vaccine by emulsifying it with an equal volume of a phosphate buffered saline solution containing 2800 CCA units/ml. of bivalent influenza virus (1600 CCA units/ml. $A_2$/Aichi/2/68 and 1200 CCA units/ml. of B/Mass./3/66).

EXAMPLE 9

Potency Test Results

Various adjuvant vaccines as described in Table III were tested for potency in guinea pigs by measuring the antibody titer 1 month post injection by standard hemaglutination inhibition tests. The results shown in Table III were obtained. It is to be noted that all the adjuvant vaccines were more potent than the aqueous vaccine in that they gave a positive hemaglutination inhibition assay result.

TABLE III

Antigenic Enhancement in Guinea Pigs of Adjuvant Emulsions of Influenza Vaccine Formulated with Various Concentrations of Pure Isomannide Monooleate or Commercial Mannide Monooleate

| Vaccine | Final Concentration Emulsifier | | Geometric Mean HI Antibody Titer at 0 and 1 month Post-Injection B/Mass./3/66 | |
|---|---|---|---|---|
|  | Commercial Mannide Monooleate | Pure Isomannide Monooleate | 0 | 1 |
| Influenza Adjuvant | 5% | — | <1:10 | 1:97 |
| Influenza Adjuvant | — | 5% | <1:10 | 1:34 |
| Influenza Adjuvant | — | 3% | <1:10 | 1:49 |
| Influenza Adjuvant | — | 1% | <1:10 | 1:320 |
| Influenza Aqueous | — | — | <1:10 | <1:10 |
| Uninoculated Controls | — | — | <1:10 | <1:10 |

Vaccine contained influenza vaccine at 300 CCA units/0.5 ml.

In addition to a water-in-oil emulsion, the novel adjuvant compositions of the invention include bimultiple systems. For example, the novel adjuvant compositions of the present invention containing pure isomannide monooleate and pure aluminum monostearate may be emulsified in an aqueous medium without destruction of the water-in-oil emulsion, resulting in the formation of the bimultiple water-in-oil-in-water (W-O-W) emulsion. Accordingly, the above described emulsions of water-in-oil (W-O) may be converted into W-O-W emulsions by the addition of an appropriate surfactant such as a 1% solution of Tween 80 to the W-O emulsion and applying appropriate force provided by devices such as turbine emulsifiers, reciprocator emulsifiers and sonication equipment, etc. In the preparation of the bimultiple system, it is preferred that additional aqueous phase be combined with the water-in-oil emulsion. The amount of aqueous phase to be included with the water-in-oil emulsion is not critical and may vary from about 10 to about 90 percent by volume based upon said water-in-oil emulsion. It may be noted that the aqueous phase may consist of any physiologically acceptable aqueous system including systems containing antigen material. The amount and type of surfactant is not critical and will vary according to the particular system involved. The resultant W-O-W emulsion contains most of the antigen in the internal or discontinuous aqueous phase. Adjuvant activity is still of the desirable W-O type but the emulsion, in addition, has a high degree of syringeability.

Procedures for the formation of bimultiple emulsions are well known in the art as illustrated by Seifriz, Jour. of Physical Chemistry, Vol. 29, page 738, (1925) and U.S. Pat. No. 3,399,263 which are incorporated herein by reference.

A representative example of bimultiple emulsion adjuvant compositions which comprise a continuous aqueous phase containing a dispersed oil phase, said dispersed oil phase consisting of a water-in-oil emulsion is as follows:

EXAMPLE 11

A composition consisting of the following ingredients was prepared:

| | Percent by volume |
|---|---|
| Adjuvant of Example 5 | 15% |
| Tween 80 | 1% |
| Phosphate buffered saline | 84% |

The Tween 80 is dissolved in the phosphate buffered saline by stirring at room temperature with a magnetic stirring bar. The emulsion of Example 5 is added to the saline solution and the probe of an ultrasonic generator was inserted to a depth of 5 mm. in the mixture. The mixture is ultrasonically agitated for 5 seconds, repeating the agitation for a total of four times. A multiple water-in-oil-in-water emulsion is formed.

While the invention has been illustraed by certain specific examples which describe the preparation of representative adjuvant vehicles and representative compositions comprising an antigen incorporated in the aqueous phase of the adjuvant vehicle, it is to be understood that modifications and variations can be made in selecting the ingredients to be combined in the preparation of these compositions within the framework of the disclosure and of the appended claims.

What is claimed is:

1. An adjuvant composition comprising a physiologically acceptable injectable oil and from about 0.5% to about 10% by volume of a stabilizer consisting essentially of aluminum monostearate, the aluminum monostearate being essentially free of any other fatty acid radical.

2. The adjuvant composition of claim 1 wherein the oil is a vegetable oil.

3. The adjuvant composition of claim 1 wherein the oil is a mineral oil.

4. The adjuvant composition of claim 2 wherein the vegetable oil is peanut oil.

5. An adjuvant vaccine composition comprising a physiologically acceptable injectable oil, an antigen and from about 0.5 to 10% by volume of stabilizer consisting essentially of aluminum monostearate, the aluminum monostearate being essentially free of any other fatty acid radical.

6. The adjuvant vaccine composition of claim 5 wherein the oil is a vegetable oil.

7. The adjuvant vaccine composition of claim 5 wherein the oil is a mineral oil.

8. The adjuvant composition of claim 6 wherein the vegetable oil is peanut oil.

9. The adjuvant vaccine composition of claim 5 wherein the antigen is influenza.

10. The adjuvant vaccine composition of claim 6 wherein the antigen is influenza.

11. The adjuvant vaccine composition of claim 8 wherein the antigen is influenza.

* * * * *